United States Patent
Kanani et al.

(10) Patent No.: US 12,326,456 B2
(45) Date of Patent: Jun. 10, 2025

(54) METHOD OF DIAGNOSIS OF THE AESTHETIC QUALITIES OF THE SKIN

(71) Applicant: L'OREAL, Paris (FR)

(72) Inventors: Sandra Kanani, Aulnay-sous-Bois (FR); Virginie Piffaut, Aulnay-sous-Bois (FR); Aude Foucher, Aulnay-sous-Bois (FR); Mark Donovan, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 785 days.

(21) Appl. No.: 16/468,073

(22) PCT Filed: Dec. 22, 2017

(86) PCT No.: PCT/EP2017/084547
§ 371 (c)(1),
(2) Date: Jun. 10, 2019

(87) PCT Pub. No.: WO2018/115517
PCT Pub. Date: Jun. 28, 2018

(65) Prior Publication Data
US 2020/0072851 A1    Mar. 5, 2020

(30) Foreign Application Priority Data
Dec. 23, 2016 (FR) ..................... 16 63364

(51) Int. Cl.
*G01N 33/68* (2006.01)
*C12Q 1/6883* (2018.01)
*G01N 33/50* (2006.01)

(52) U.S. Cl.
CPC ....... *G01N 33/6881* (2013.01); *C12Q 1/6883* (2013.01); *G01N 33/5044* (2013.01); *C12Q 2600/148* (2013.01); *C12Q 2600/158* (2013.01); *G01N 2500/04* (2013.01); *G01N 2500/10* (2013.01); *G01N 2800/20* (2013.01)

(58) Field of Classification Search
None
See application file for complete search history.

(56) References Cited

U.S. PATENT DOCUMENTS

2010/0216165 A1    8/2010   Donovan et al.

FOREIGN PATENT DOCUMENTS

| DE | 102009046128 | * | 8/2009 | ............ C12Q 1/02 |
|---|---|---|---|---|
| JP | 2011-085491 A | | 4/2011 | |
| JP | 2014-206488 A | | 10/2014 | |
| JP | 2015-158500 A | | 9/2015 | |
| KR | 10 2014 0123437 | | 10/2014 | |
| WO | WO 2015/158765 A1 | | 10/2015 | |

OTHER PUBLICATIONS

Makino et al., Journal of Dermatological Science 84 (2016) e89-e180; p. e138 (Year: 2016).*
Kandelwal et al., Biol Blood Marrow Transplant 19 (2013) S313-S341, abstract #444 (Year: 2013).*
Aziz et al., Cosmeceuticals and Natural Cosmetics, Dec. 2017; In book: Recent Trends in Malaysia Medicinal Plants Research (pp. 126-175) Publisher: UTM Press (Year: 2017).*
Adnan Nasir, MD, Cosmetic Dermatology, 2009; 22: 139-145 (Year: 2009).*
Geffré et al., Veterinary Clinical Pathology, 2009, 38: 288-298 (Year: 2009).*
The NLB Appendix by Chang et al. (Rockville (MD): Agency for Healthcare Research and Quality (US); Jun. 2012. Appendix: Test Performance Metrics. Available from: https://www.ncbi.nlm.nih.gov/books/NBK98249/ (Year: 2012).*
Machine translation of DE102009046128, original document published Aug. 5, 2009 (Year: 2009).*
Pendaries et al., "In a three-dimensional reconstructed human epidermis filaggrin-2 is essential for proper cornification", Cell Death and Disease (2015) 6, e1656; 9 pages; doi:10.1038/cddis.2015.25.
Wu et al., "Molecular Identification and Expression Analysis of Filggrin-2, a Member of the S100 Fused-Type Protein Family", Plos One, vol. 4, No. 4, Apr. 2009.
Pellelrin et al., "Abstracts of the Annual Congress of the French-Speaking Society for Dermatological Research", Journal of Investigative Dermatology (2011) 131, 2143-2154.
Boccardo et al., "Comparative proteomic profiling of patients with atopic dermatitis based on history of eczema herpeticum infection and *Staphylococcys aureus* colonization", J. Allergy Clin Immunol, Jan. 2011, vol. 127, No. 1, pp. 186-193.
Sagayaraj, "D Squame Tape stripping tutorial", Jun. 21, 2016 URL:https://www.youtube.com/watch?v-wdEBITHTEUg [retrieved Oct. 5, 2017].

* cited by examiner

*Primary Examiner* — Christina M Borgeest
(74) *Attorney, Agent, or Firm* — POLSINELLI PC

(57) ABSTRACT

The present invention relates to a method for diagnosing a degradation of esthetic qualities of the skin, based on a measurement of the level of expression of the gene encoding FLG2. The present invention also relates to a method for the cosmetic treatment of skin. The present invention also relates to a method for identifying a compound for reducing and/or slowing the degradation of esthetic quality of the skin, and a kit.

2 Claims, No Drawings

METHOD OF DIAGNOSIS OF THE AESTHETIC QUALITIES OF THE SKIN

CROSS REFERENCE TO RELATED APPLICATIONS

This application is a National Phase filing under 35 U.S.C. § 371 of PCT/EP2017/084547 filed on 22 Dec. 2017; which application in turn claims priority to Application No. 16 63364 filed in France on 23 Dec. 2016. The entire contents of each application are hereby incorporated by reference.

This invention relates to methods for diagnosing esthetic qualities of the skin.

Esthetic qualities of the skin can be degraded following different types of damage caused by functional and structural changes and degradations of all its compartments (epidermis, dermo-epidermic junction, dermis, dermo-hypodermic and hypodermic junction). Many metabolic functions can be affected at the cell level. The epidermis becomes thinner, keratinocytes lose their ability for renewal and repair, synthesis of hyaluronic acid, proteoglycanes, the quality and cohesion of the dermo-epidermic junction are reduced making the skin tissue thinner and more fragile, the epidermis becomes thinner, and the dermo-epidermis junction loses its invaginations. The same applies at the dermic level at which fibroblasts synthesize fewer proteins or fundamental matrix molecules in its organization (collagens, particularly proteoglycanes). The hypodermis is also affected. All these events weaken the entire skin and make it less firm, less elastic, more fragile and it becomes difficult for it to retain a correct level of moisturization. The skin can also lose its radiance and there are modifications to its microrelief leading to the appearance of roughness, wrinkles and lentigos, all of which are signs of "bad condition" or fatigue. Furthermore, the change to all skin properties can be exacerbated by different secondary factors such as the consequence of environmental aggression such as pollution, extrinsic factors such as tobacco, variations in the organization and density of the hypodermis subsequent to a change in the body mass, pregnancy, obese state, cellulitis, or the disorganization of constituents of the extracellular matrix, for example resulting from stretch marks, scars.

From the above, it is easy to understand the importance of finding biomarkers that can be used to detect signs of degradation of the esthetic properties of the skin, particularly when they are not yet visible, so as to be able to reduce and/or slow degradation to the esthetic qualities of the skin. In particular, there is an important need for biomarkers specific to one or more of these signs, so as to be able respond in a suitable manner for a given subject. The aim of the invention is to meet this need.

The applicant surprisingly discovered that the expression of the gene encoding la Filaggrin 2 (FLG2), at the level of the skin, is correlated with the esthetic qualities of the skin, and particularly the shine, the rough texture and flaccidity of the skin.

Filaggrin 2 (FLG2), also known under the name of ifapsoriasin (IFPS), is a member of the S100 proteins family. This is a 250 kDa protein, rich in histidine and glutamine, composed of 2391 amino acids. FLG2 is expressed at its messenger RNA (mRNA), in the skin, the thymus, the stomach, the testicles and the placenta. FLG2 is expressed in the stratum granulosum and in the basal stratum corneum of human skin.

Thus, according to a first of its aspects, the invention relates to a method for diagnosis, preferentially in vitro, of a degradation to the esthetic qualities of the skin in a subject, said method comprising the following steps:
  a) measure the level of expression of the gene encoding FLG2, in a skin sample from said subject, and
  b) optionally, on the basis of the level of expression of the gene encoding FLG2 measured in step a), determine whether said subject's skin displays degraded esthetic qualities.

This invention also relates to a method for the cosmetic treatment of a skin for which the esthetic qualities are degraded in a subject, said method comprising the following steps:
  a) measure the level of expression of the gene encoding FLG2, in a skin sample from said subject;
  b) from step a), infer whether said subject's skin displays degraded esthetic qualities;
  c) if the skin is identified as displaying degraded esthetic qualities in step b), treat said skin with a cosmetic composition suitable for reducing and/or slowing the degradation of the esthetic qualities of the skin.

"Degradation of esthetic qualities of the skin" means any changes to the skin that degrade its esthetic appearance and that are not always visible at the early stages, particularly the reduction in shine and/or appearance of a rough texture and/or an increase in the flaccidity of the skin, preferably facial skin, and particularly cheeks and/or the forehead.

"Skin shininess" as used in this description refers to skin with good brightness, and/or not dull skin, and/or a radiant complexion.

FLG2 is a protein for which the sequence of amino acids is known and that in particular corresponds to the sequence with the NCBI accession code: NP_001014364.1 (Dec. 11, 2015 version). The mRNA sequence encoding FLG2 is also known to those skilled in the art and particularly accessible with the NCBI accession code: NM_001014342.2 (Dec. 11, 2015 version).

The term "level of expression of the gene encoding FLG2" denotes the level of expression of messenger RNA (mRNA) of the gene encoding FLG2 and/or the level of expression of FLG2 protein.

Preferably, the level of expression of FLG2 protein is measured using a specific ligand of FLG2 protein, such as for example an antibody, preferably monoclonal, an Fab fragment, an scFv or a nanobody, specific for this protein. The level of expression may then be measured by means of any method known to those skilled in the art, such as for example by means of an ELISA test, preferably a sandwich ELISA test using a capture antibody, specific for FLG2 protein and a detection antibody, also specific for FLG2 protein. In particular, the measurement of the level of expression of FLG2 protein may be made using a miniaturized system such as a microfluidic chip, such as that described in the international application WO2011/126249, this chip containing specific ligands for FLG2 protein. The chip may subsequently be analyzed by means of a suitable reader in order to determine whether FLG2 proteins have bonded with said ligand and to reach a conclusion regarding the presence and the quantity of FLG2 in the skin sample.

Preferably, the level of expression of mRNA of the gene encoding FLG2 is measured using a complementary nucleotide sequence of the mRNA of the gene encoding FLG2 and specifically hybridizing with the mRNA of the gene encoding FLG2 or, a fragment thereof hybridizing specifically with the mRNA of the gene encoding FLG2, this sequence or this fragment comprising 5 to 50 nucleotides, preferentially 10 to 20 nucleotides, or using a pair of primers or a probe of 10 to 60 nucleotides, preferentially 15 to 30 nucleotides comprising said sequence or said fragment. The level of expression may then be measured by any means known to those skilled in the art, for example by means of quantitative PCR.

Within the scope of the invention, the terms "hybridize" or "hybridization", as well-known to those skilled in the art, refer to the bonding of a nucleic acid sequence with a particular nucleotide sequence under suitable conditions, particularly under stringent conditions.

The term "stringent conditions", as used herein, corresponds to conditions which are suitable for producing bond pairs between the nucleic acids having a defined level of complementarity, while being unsuitable for the formation of pairs between the bonding nucleic acids having a lower complementarity than said defined level. The stringent conditions are dependent on hybridization and washing conditions. These conditions may be modified according to methods known to those skilled in the art. Generally, high-stringency conditions are a hybridization temperature approximately 5° C. less than the melting point (Tm), preferably close to the Tm of the perfectly base-paired strands. The hybridization procedures are well-known in the art.

High-stringency conditions generally involve hybridization at a temperature of approximately 50° C. to approximately 68° C. in a 5×SSC/5×Denhardt's solution/1.0% SDS solution, and washing in a 0.2×SSC/0.1% SDS solution at a temperature between approximately 60° C. and approximately 68° C.

According to one preferred embodiment, the skin sample of the subject used in the methods according to the invention, is a sample taken, preferably non-invasively, on the subject's skin, preferentially on the subject's face, in particularly on the subject's cheek. Preferably, the skin sample is obtained from the stratum corneum. Preferably, the skin sample is taken from an area with no lesions.

The stratum corneum is the outermost layer of the epidermis, and comprises the skin surface. It is essentially made up of dead cells.

According to one embodiment, the methods according to the invention comprise a step for taking the skin sample from the subject. This step is preferably performed non-invasively, and in particular does not require local anesthetic. According to one preferred embodiment, the step for taking the sample is performed by rubbing the skin surface or using an adhesive surface such as a D-Squame® disc.

The term "subject" denotes a human being, preferably aged from 20 to 90 years, preferentially from 35 to 80 years, from 45 to 80 years and even more preferentially from 60 to 80 years. Preferably, the subject is female. Preferably, the subject does not suffer from dermatological lesions and/or a dermatological pathology.

According to one embodiment, the reference value is between 140 and 190 ng/ml of FLG2 for the shine, According to one embodiment, the reference value is between 122 and 166 ng/ml of FLG2 for the roughness texture, According to one embodiment, the reference value is between 82 and 112 ng/ml of FLG2 for the flaccidity.

In one particular embodiment, step (b) is carried out after comparing the level of expression after comparing the level of expression of the gene encoding FLG2 obtained with at least one reference value. In one embodiment, the reference value can be determined by the mean value of the level of expression of the gene encoding FLG2 in a defined population, for example a population in a defined age-group and/or having a defined skin type (Caucasian, Asian, etc.). In one particular embodiment, the reference value is determined by the mean value of the level of expression of the gene encoding FLG2 in women aged from 60 to 80 years. In another embodiment, the reference value is the optimal threshold value determined by ROC analysis. In particular, the reference can vary depending on the sign of degradation of the esthetic qualities of the skin considered. According to the invention, a reference value may be determined by a plurality of samples, preferably more than 50, 100, 200, 300 or 500 samples. In one embodiment, two reference values are used. These values can then determine a range around the mean value of the level of expression of the gene encoding FLG2 in a defined population, for example a population in a defined age-group and/or having a defined skin type (Caucasian, Asian, etc. or a skin with a greasy tendency, dry skin, etc.). In one particular embodiment, the reference values are determined by the mean value of the level of expression of the gene encoding FLG2 plus or minus the standard deviation of the level of expression of the gene encoding FLG2 in women aged from 30 to 80 years. In another embodiment, the reference values are the optimal threshold values determined by ROC analysis.

The term "comparison" refers to the fact of determining whether the level of expression of the gene encoding FLG2 is essentially identical to or is different from a reference value, particularly when there is only one reference value. Preferably, the level of expression of the gene encoding FLG2 is considered to be different from a reference value if the observed difference is statistically significant. If the difference is not statistically significant, the level of expression of the gene encoding FLG2 and the reference value are essentially identical.

On the basis of this comparison, it is possible to determine whether the skin displays degraded esthetic qualities. Typically, the skin is considered to display degraded esthetic qualities when the level of expression of the gene encoding FLG2 is significantly higher than and/or lower than the reference value and the skin is not considered to display degraded esthetic qualities when the level of expression of the gene encoding FLG2 is essentially identical to the reference value.

In particular, the skin is considered to display degraded esthetic qualities, particularly such as the appearance of a rough texture, when the level of expression of the gene encoding FLG2 is significantly lower than the reference value for this sign and the skin is not considered to display degraded esthetic qualities, particular such as the appearance of a rough texture, when the level of expression of the gene encoding FLG2 is essentially identical to the reference value.

In particular, the skin is considered to display degraded esthetic qualities, particularly such as a reduction of the shine or an increase of the flaccidity, when the level of expression of the gene encoding FLG2 is significantly higher than the reference value for each of these signs and the skin is not considered to display degraded esthetic qualities, particular such as a reduction of the shine or an increase of the flaccidity, when the level of expression of the gene encoding FLG2 is essentially identical to the reference value.

The term "comparison" also refers to the fact of determining whether the level of expression of the gene encoding FLG2 is essentially inside or outside the range defined by two reference values. Preferably, the level of expression of the gene encoding FLG2 is considered to be outside the range if, in addition to being outside the range, the observed difference between the measured expression level and the closest reference value is statistically significant. If the difference is not statistically significant, the level of expression of the gene encoding FLG2 is considered to be inside the range of values.

On the basis of this comparison, it is possible to determine whether the skin displays degraded esthetic qualities. Typically, the skin is considered to display degraded esthetic qualities when the level of expression of the gene encoding FLG2 is essentially outside the range defined by the two reference values and the skin is not considered to display degraded esthetic qualities when the level of expression of the gene encoding FLG2 is essentially within the range defined by the two reference values.

The term "cosmetic composition suitable for reducing and/or slowing degradation of esthetic qualities of the skin" denotes any cosmetic composition known to those skilled in the art suitable for reducing and/or slowing the degradation of esthetic qualities of the skin such as a reduction in the shine, the appearance of a rough texture and an increase in the flaccidity of the skin.

The invention also relates to a method for identifying a compound suitable for reducing and/or slowing the degradation of esthetic qualities of the skin, said method comprising the following steps:
a) measure the level of expression of the gene encoding FLG2, in a skin sample exposed to said candidate compound;
b) compare said level of expression to the level of expression in a sample of said skin not exposed to said compound;
c) identify said candidate compound as a compound suitable for reducing and/or slowing the degradation of esthetic qualities of the skin when a variation in the level of expression of the gene encoding FLG2 in the skin sample exposed to said candidate compound is detected, with respect to the level of expression of the gene encoding FLG2 in the skin sample not exposed to the candidate compound.

According to one preferred embodiment, said candidate compound is identified as a compound suitable for reducing and/or slowing the degradation of esthetic qualities of the skin, particularly reducing and/or slowing the appearance of a rough texture, when an increase in the level of expression of the gene encoding FLG2 in the skin sample exposed to said candidate compound is detected, with respect to the level of expression of the gene encoding FLG2 in the skin sample not exposed to the candidate compound.

According to another preferred embodiment, said candidate compound is identified as a compound suitable for reducing and/or slowing the degradation of esthetic qualities of the skin, particularly reducing and/or slowing the reduction in the shine and/or the increase in the flaccidity of the skin, when an increase in the level of expression of the gene encoding FLG2 in the skin sample exposed to said candidate compound is detected, with respect to the level of expression of the gene encoding FLG2 in the skin sample not exposed to the candidate compound.

According to one preferred embodiment, the skin sample used in the method for identifying a compound suitable for reducing and/or slowing the progression of the degradation of esthetic qualities of the skin according to the invention is a skin cell culture, an epidermis culture, a reconstructed whole skin, a human skin explant, or a skin sample from a subject as defined above.

Preferentially, the methods according to the invention comprise a step for treating the sample so as to prepare the measurement of the level of expression of the gene encoding FLG2. For example, the treated sample is a soluble protein extract. In particular, if the skin sample has been obtained using an adhesive surface such as a D-Squame® disc, the soluble protein extract may be obtained using a protein extraction system such as that described in the international application WO2015/009085 which is suitable for bringing the D-squame samples into contact with a minimal volume of extraction buffer and thereby obtaining a soluble protein extract.

The present invention also relates to a kit comprising:
a) means for measuring the expression of the gene encoding FLG2 in a skin sample, and
b) an instruction leaflet.

The term "means for measuring the expression of the gene encoding FLG2" denotes a specific ligand of FLG2 protein, such as for example an antibody, preferably monoclonal, an Fab fragment, an scFv or a nanobody, specific for this protein or a microfluidic chip such as that described in the international application WO2011/126249, this chip containing specific ligands for FLG2 protein. Alternatively, it denotes a complementary nucleotide sequence of the mRNA of the gene encoding FLG2 and specifically hybridizing with the mRNA of the gene encoding FLG2 or, a fragment thereof hybridizing specifically with the mRNA of the gene encoding FLG2, this sequence or this fragment comprising 5 to 50 nucleotides, preferably 10 to 20 nucleotides, or a pair of primers or a probe of 10 to 60 nucleotides, preferentially 15 to 30 nucleotides comprising said sequence or said fragment.

According to one embodiment, the kit according to the invention also comprises a standard range for the expression of the gene encoding FLG2.

Preferably, the means for measuring the expression of the gene encoding FLG2 is at least one specific ligand of FLG2, in particular a pair of capture and detection antibodies specific to FLG2 protein.

According to one embodiment, the kit according to the invention also comprises means for taking the skin sample such as a D-Squame® disc.

The present invention also relates to the use of a kit according to the invention for identifying a compound suitable for reducing and/or slowing the progression of degradation of esthetic qualities of the skin.

The present invention will be illustrated by the following example.

EXAMPLE

The reduction in the shine, roughness and flaccidity were evaluated on the cheeks of 376 women aged 36 to 75 years. The level of protein expression of the gene encoding FLG2 was also evaluated on these women's cheeks, by means of a D-Squame® sample wherein the soluble protein extract was analyzed using an ELISA test conducted on a chip.

The univariate statistical analysis of the results obtained shows a correlation between the degradation of esthetic qualities of the skin and the expression of FLG2. In particular, beyond the threshold values defined for flaccidity and for shine in Table 1, the skin is likely to evolve towards a flaccid skin or lose its shine, respectively. Below the threshold values defined for roughness in Table 1, the skin is likely to evolve towards a rough skin.

TABLE 1

| Clinical sign | Accuracy | Sensitivity | Specificity | Threshold value (in ng/ml) | p-values |
|---|---|---|---|---|---|
| Shine | 66% | 77% | 53% | 166 | <0.001 |
| Roughness | 63% | 72% | 53% | 144 | <0.001 |
| Flaccidity | 58% | 64% | 51% | 97 | |

The invention claimed is:

1. A method for cosmetic treatment of a skin for which the esthetic qualities are degraded in a subject, wherein the degraded esthetic qualities are selected from the reduction in shine, appearance of a rough texture, or an increase in skin flaccidity in a subject, wherein the subject does not suffer from dermatological lesions or a dermatological pathology, said method comprising the following steps:
   a) measuring the level of expression of the gene encoding FLG2 in a skin sample from said subject; wherein the level of expression of the gene encoding FLG2 is determined by measuring the level of expression of the protein encoded by the gene;
   b1) determining that the level of expression of the gene encoding FLG2 measured in step a) is statistically lower than a reference value, wherein the reference value is about 166 ng/ml of FLG2; and
   c1) treating the skin of the subject with a statistically lower expression level than the reference value with a cosmetic composition suitable for treating rough texture of the skin of the subject; or
   b2) determining that the level of expression of the gene encoding FLG2 measured in step a) is statistically higher than a reference value, wherein the reference value is about 140 ng/ml of FLG2 for shine and wherein the reference value is about 82 ng/ml of FLG2 for the flaccidity; and
   c2) treating the skin of the subject with a statistically higher expression level than the reference value with a cosmetic composition suitable for treating a reduction in the shine and/or an increase in the flaccidity of the skin of the subject.

2. The method according to claim 1, in which the skin sample is taken using an adhesive surface.

* * * * *